US 6,777,679 B2

(12) United States Patent
Nagaoki et al.

(10) Patent No.: US 6,777,679 B2
(45) Date of Patent: Aug. 17, 2004

(54) METHOD OF OBSERVING A SAMPLE BY A TRANSMISSION ELECTRON MICROSCOPE

(75) Inventors: Isao Nagaoki, Hitachinaka (JP); Hiroyuki Kobayashi, Mito (JP); Takafumi Yotsuji, Hitachinaka (JP); Toshiyuki Ohyagi, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 10/353,039

(22) Filed: Jan. 29, 2003

(65) Prior Publication Data

US 2003/0183762 A1 Oct. 2, 2003

(30) Foreign Application Priority Data

Mar. 27, 2002 (JP) ..................... 2002-089578

(51) Int. Cl.[7] .............................. H01J 37/26
(52) U.S. Cl. ..................... 250/311; 250/306
(58) Field of Search ................. 250/306, 307, 250/310, 311, 397

(56) References Cited

U.S. PATENT DOCUMENTS

| 4,851,674 A | * | 7/1989 | Kobayashi | 250/311 |
| 5,001,345 A | * | 3/1991 | Suzuki | 250/311 |
| 6,218,663 B1 | * | 4/2001 | Nisch et al. | 250/309 |
| 6,472,663 B2 | * | 10/2002 | Nagaoki et al. | 250/311 |
| 6,573,502 B2 | * | 6/2003 | Kondo | 250/311 |
| 6,617,580 B2 | * | 9/2003 | Voelkl | 250/311 |

FOREIGN PATENT DOCUMENTS

JP 2001-118535 4/2001

* cited by examiner

Primary Examiner—John R. Lee
Assistant Examiner—Johnnie L Smith, II
(74) Attorney, Agent, or Firm—Dickstein Shapiro Morin & Oshinsky LLP

(57) ABSTRACT

Automatically corrected is a movement of a field of view caused upon changing a magnification. A field of view is searched for with a first magnification. A sample stage coordinate of a designated subject of recording is computed, for storage, on a transmission electron beam image of a sample displayed on an image display section. A subject-of-recording image is cut out of the transmission electron beam image of the sample in the first magnification and stored as a first image. The magnification of the transmission electron microscope is set to a magnification twice a magnification in the recording mode, to move the sample stage to the stored sample stage coordinate of the subject of recording. The transmission electron beam image in the second magnification is captured with the same number of pixels as the first image to compute a movement amount of between the two images from a correlation intensity of the first and second images. Then, the transmission electron beam image in the second magnification is corrected in position with respect to imaging means such that the movement amount is zero, to store an obtained transmission electron beam image (S29).

7 Claims, 12 Drawing Sheets

CENTER COORDINATE (X1, Y1) OF OBSERVING FIELD OF VIEW

SAMPLE CENTER (0, 0)

2048 pixel 2048 pixel

FOCUS REGION (X3, Y3)

METHOD OF OBSERVING A SAMPLE BY A TRANSMISSION ELECTRON MICROSCOPE

BACKGROUND OF THE INVENTION

1. Field of the Invention

The present invention relates to a method of observing a magnified image and, more particularly, to a method of observing a magnified image of a sample by the use of a transmission electron microscope.

2. Description of the Related Art

The transmission electron microscope is for focusing an electron beam transmitted through a sample interior, making it possible to observe an interior structure of the sample. With the transmission electron microscope, it is possible to observe lattice defects and grain-boundary structure of a material, precipitate size and distribution or lattice images.

Concerning a transmission electron beam image of a sample by the transmission electron microscope, the field of view is not always coincident at between low magnification and high magnification even at the same coordinate of position. This is because the transmission electron microscope image undergoes the effects of a hysteresis native to a lens, thermal drift on a sample and axis deviation caused upon magnification change and hence the field of view is moved in position by a change of observing magnification.

It is an object of the present invention to provide a method of observing a sample which can automatically correct a movement in view field caused upon changing a magnification, in view of the foregoing problem to be encountered in observing a sample magnified image by using a transmission electron microscope.

SUMMARY OF THE INVENTION

A method of observing a sample by a transmission electron microscope, for achieving the foregoing object, according to the present invention comprises: a step of inputting a first magnification for use in searching a field of view and a second magnification for use in recording; a step of setting a magnification of a transmission electron microscope to the first magnification; a step of imaging a transmission electron beam image of a sample held on a sample stage by imaging means and displaying the transmission electron beam image of the sample in the first magnification on an image display section; a step of computing and storing a sample stage coordinate of a subject of recording designated over the transmission electron beam image of the sample displayed on the image display section; a step of cutting an image of the subject of recording out of the transmission electron beam image of the sample in the first magnification and storing a cut-out image as a first image; a step of setting the magnification of the transmission electron microscope to the second magnification; a step of moving the sample stage to the stored sample stage coordinate of the subject of recording; a step of capturing the transmission electron beam image in the second magnification with the same number of pixels as the first image and storing a captured image as a second image; a step of computing a movement amount of between the two images from a correlation intensity of the first and second images; a step of correcting a position of the transmission electron beam image in the second magnification with respect to the imaging means such that the movement amount is zero; and a step of recording the transmission electron beam image in the second magnification imaged by the imaging means.

Herein it is preferred to further comprise a step of computing a size of a region on the sample to be recorded in the second magnification over the transmission electron beam image of the sample in the first magnification, and a step of displaying a mark representing a region in a computed size by being superposed over a corresponding area of the transmission electron beam image in the first magnification.

A method of observing a sample by a transmission electron microscope comprises: a step of inputting a first magnification for use in searching a field of view; a step of setting a magnification of a transmission electron microscope to the first magnification; a step of imaging a transmission electron beam image of a sample held on a sample stage by imaging means and displaying the transmission electron beam image in the first magnification on an image display section; a step of acquiring information concerning a recording region designated over the transmission electron beam image of the sample displayed on the image display section; a step of computing and storing a sample stage coordinate of the recording region and a second magnification capable of putting the recording region fully in a field of view from the acquired information; a step of cutting an image in the recording region out of the transmission electron beam image of the sample in the first magnification and storing a cut-out image as a first image; a step of setting the magnification of the transmission electron microscope to the second magnification; a step of moving the sample stage to the stored sample stage coordinate of the recording region; a step of capturing the transmission electron beam image in the second magnification with the same number of pixels as the first image and storing a captured image as a second image; a step of computing a movement amount of between the two images from a correlation intensity of the first and second images; a step of correcting a position of the transmission electron beam image in the second magnification with respect to the imaging means such that the movement amount is zero; and a step of recording the transmission electron beam image in the second magnification imaged by the imaging means.

It is possible to designate a recording region on the transmission electron beam image of the sample displayed on the image display section, for example, by clicking two diagonal points of a rectangular recording region with using a mouse or dragging a rectangular frame representing a recording region with using a mouse.

The transmission electron beam image in the second magnification with respect to the imaging means can be corrected in position by moving the sample stage or deflecting an electron beam transmitted through the sample with using a sample image moving coil.

It is preferred to further comprise a step of determining a movement amount of an image when an electron beam to be irradiated to the sample is inclined by a predetermined angle, and a step of correcting an objective current value on the basis of the movement amount of the image thereby correcting for focusing of an objective lens.

The movement amount between the two images may be displayed on the image display section.

The sample observing method of the invention has the following features:

1) a recording object can be coordinate-displayed on an image taken with a low magnification;
2) a recording region can be graphic-displayed on an image taken with a low magnification;
3) an observation field of view can be automatically corrected; and
4) a focus can be automatically corrected.

DETAILED DESCRIPTION OF THE PREFERRED EMBODIMENTS

Embodiments of the present invention will now be explained with reference to the drawings.

Figure 1:
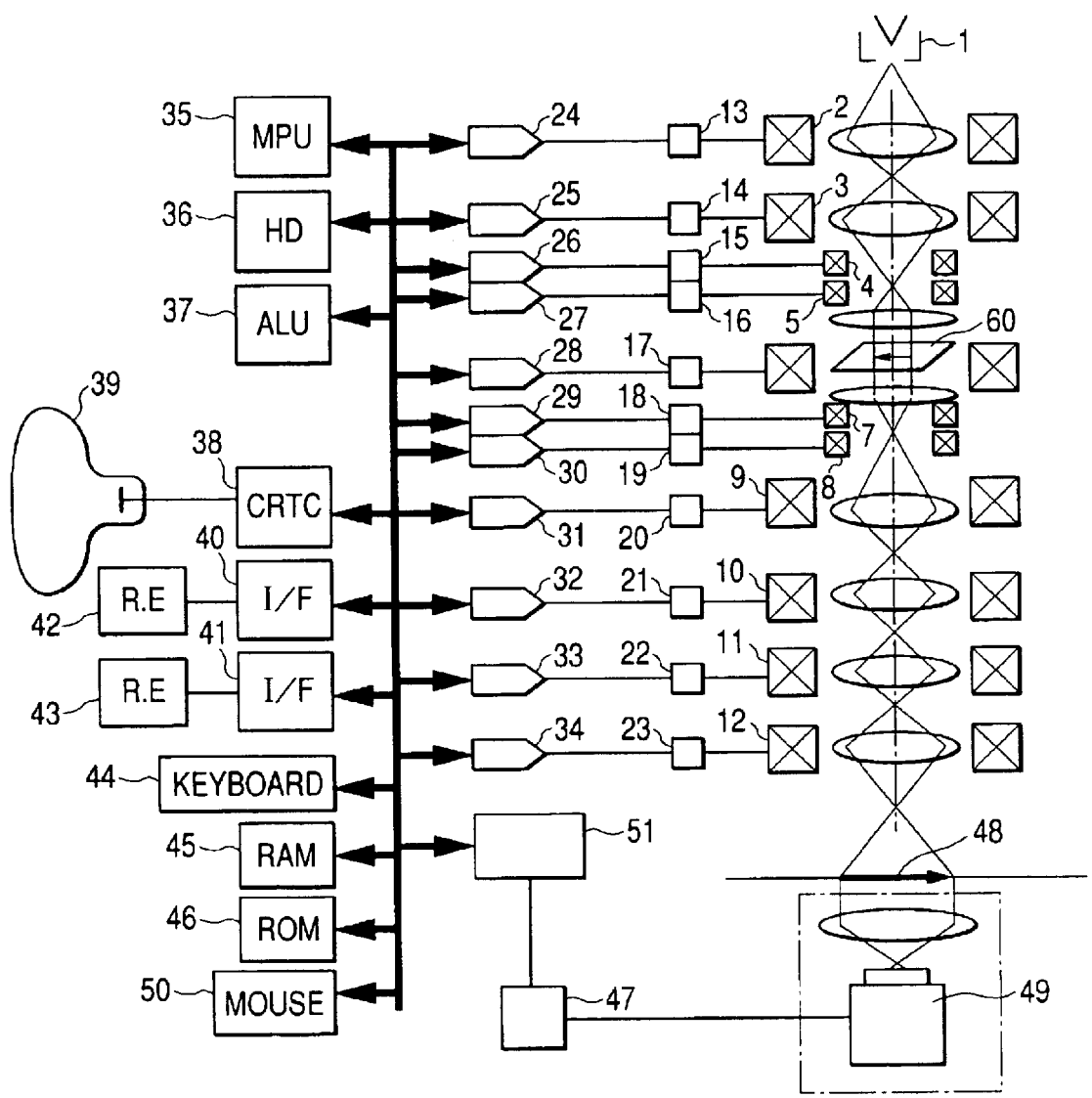
FIG. 1 is a schematic functional block diagram of one example of a transmission electron microscope for use in the present invention.

FIG. 1 is a schematic functional block diagram of one example of a transmission electron microscope to be used in the invention. Note that, although a deflection coil is regardless of the number of stages, explanation is herein made on a transmission electron microscope using a two-staged deflection coil in general use. Hereinafter, the operation mode for searching an observation field of view is referred to as an observing mode, the operation mode for focus adjustment is as a focus mode, and the operation mode for imaging a sample image is as a recording mode.

The accelerated electron beam emanated from the electron gun 1 is converged by a first irradiation lens 2 and second irradiation lens 3 and deflected by a first deflection coil 4 and second deflection coil 5 to be focused by an objective lens 6, thus irradiated onto a sample held on a sample stage 60. The electron beam transmitted through the sample passes a first electromagnetic sample image moving coil 7 and second electromagnetic sample image moving coil 8 and then magnified by a first intermediate lens 9 and second intermediate lens 10, and thereafter further magnified by a first projection lens 11 and second projection lens 12 to form a sample transmission image on a scintillator 48. The transmission electron image of the sample, converted into an optical image by the scintillator 48, is imaged by a TV camera (imaging device) 49. The video signal from the TV camera 49 is captured through a TV camera control section 47 and image capturing interface 51 into the microprocessor 35 where it is processed, thereafter being displayed on a CRT 39 under control of a CRT controller 38. The microprocessor 35 controls excitation power sources 13–23 to feed power to the lenses 2–12 of the electron microscope, through DACs 24–34. Also, the microprocessor 35 is connected, through a bus, with a storage device 36 such as a hard disk, an operating device 37, magnification-switching rotary encoder 42, an inputting rotary encoder 43, a keyboard 44, a RAM 46, a ROM 47, a mouse 50 and so on. The rotary encoder 42, 43 is connected to the bus through an I/F 40, 41.

Figure 2:
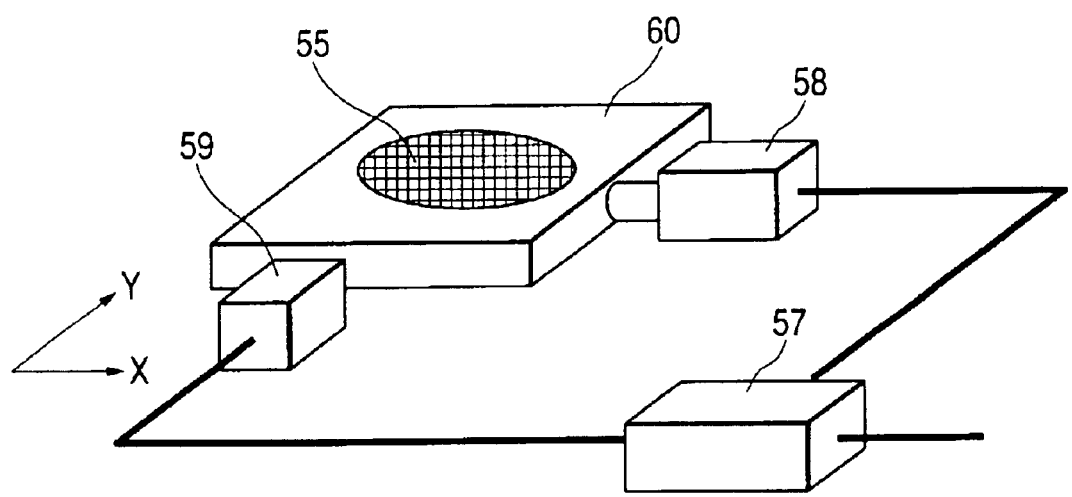
FIG. 2 is an explanatory view of a sample stage.

FIG. 2 is a concept view of the sample stage for holding a sample thereon. The sample stage 60 has a mesh-like sample-resting surface 55 so that a sample can be held on the sample-resting surface 55. The sample stage 60 is to be driven in X and Y directions by an X-direction drive motor 58 and a Y-direction drive motor 59 that are under drive-control of a sample stage controller 57, according to an instruction from the microprocessor 35. The sample held on the sample stage 60 is moved to a desired position with respect to the axis of an electron beam, to select an observation field of view.

Figure 3:
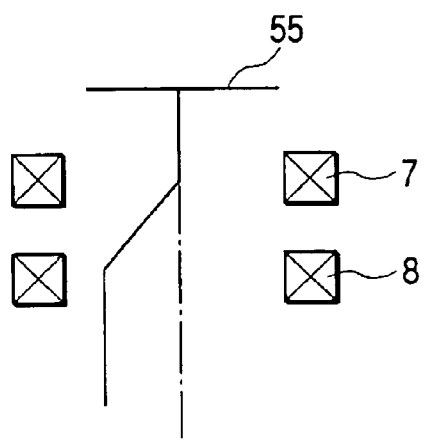
FIG. 3 is a concept view of an electronic sample image moving mechanism.

FIG. 3 is a concept view of the electronic sample image moving mechanism. The electronic sample image moving mechanism has a first electromagnetic sample image moving coil 7 and a second electromagnetic sample image moving coil 8. Using the two coils, a sample-transmitted electron beam is deflected whereby a sample image can be shifted without inclining the axis of the electron beam.

In case a field of view is moved by moving the sample stage, movement amount can be taken great but movement accuracy cannot be enhanced so high. On the other hand, in case the electronic sample image moving mechanism is used, movement amount is small but a view field can be microscopically moved with accuracy. In moving a view field, the sample stage may be used in accordance with a situation or the electronic sample image moving mechanism may be used. Otherwise, the both may be employed.

Explanation will be now made on an element art employed in a sample observing method using a transmission electron microscope of the invention.

(1) Correcting a Movement Amount of Between Two Images

Figure 4:
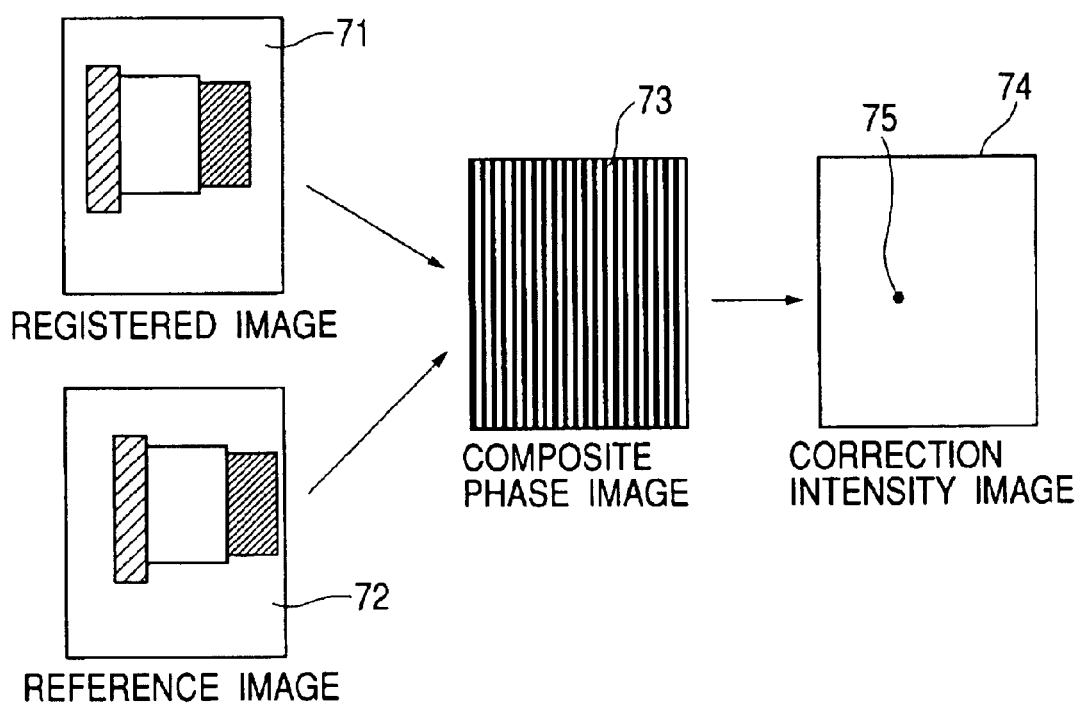
FIG. 4 is an explanatory view of an image correlation.

Explanation will be made on correcting a movement amount (deviation amount) of between two images by using an example of an image correlation shown in FIG. 4. A transmission electron microscope image 1 is cut in part into a transmission image 3, and the transmission image 3 is recorded as a registered image $f1(m, n)$ with the number of pixels M×N to a storage device 36. Next, a transmission electron microscope image 2 captured after switching into a recording mode is recorded as a reference image $f2(m, n)$ with the number of pixels M×N to the storage device. Note that the both are natural images wherein m=0, 1, 2, ..., M−1; n=0, 1, 2, ..., N−1.

The discrete Fourier images $F1(u, v)$ and $F2(u, v)$ of the registered image $f1(m, n)$ and reference image $f2(m, n)$ are respectively defined by the following Equations (1) and (2). Note that u=0, 1, 2, ..., M−1; v=0, 1, 2, ..., N−1, wherein $A(u, v)$ and $B(u, v)$ are amplitude spectrums and $\theta(u, v)$ and $\phi(u, v)$ are phase spectrums.

[Equation 1]

$$F1(u, v) = A(u, v)e^{j\theta(u,v)} \quad (1)$$

$$F2(u, v) = B(u, v)e^{j\phi(u,v)} \quad (2)$$

In phase correlation, where there is a parallel movement between the two images, a correlation peak position deviates by a movement amount. Explanation is made below on how to derive the movement amount. First, $f4(m, n) = f2(m+r', n)$ is provided on an assumption that an original image $f2(m, n)$ has moved by r' in an m-direction. The foregoing Equation (2) is transformed into Equation (3).

[Equation 2]

$$F4(u, v) = \Sigma\Sigma f2(m + r', n)e^{-j2\pi(mu/M + nv/N)}$$
$$= B(u, v)e^{j(\phi + 2\pi r'u/M)}$$ (3)

By taking the amplitude spectrum B(v, v) as a constant, a phase image is not relied upon an image contrast. The phase image $F'4(u, v)$ of f4 is given by the following Equation (4).

[Equation 3]

$$F'4(u, v) = e^{j(\phi + 2\pi r'u/M)}$$ (4)

By multiplying a complex conjugate of $F'2(u, v)$ on the phase image $F'1(u, v)$, obtained is a composite image $H14(u, v)$ as expressed by the following Equation (5).

[Equation 4]

$$H14(u, v) = F'1(u, v) (F'2(u, v))^*$$
$$= e^{j(\theta - \phi - 2\pi ru/M)}$$ (5)

A correlation intensity image $G14(r, s)$ is turned into the following Equation (6) by inversely Fourier-transforming the composite image $H14(u, v)$.

[Equation 5]

$$G14(r, s) = \Sigma\Sigma(H14(u, v))e^{j2\pi(ur/M + us/N)}$$
$$= \Sigma\Sigma(e^{j(\theta - \phi - 2\pi r'u/M)})e^{j2\pi(ur/M + us/N)}$$
$$= G12(r - r')$$ (6)

From equation (6), where there is an amount r' of positional deviation in the m-direction between the wo images, the peak of the correlation intensity image deviates in position by −r'. Meanwhile, because of making a correlation computation with a phase component, a movement amount can be computed even where there is difference in brightness or contrast between the two images. In the case that a positional deviation exists in the m-direction between the two images, a peak occurs in a position of ΔG(pixel) with respect to a center of the correlation intensity image. For example, as shown in FIG. 4, in case there is a deviation of 2-pixels in the m-direction at between two images 71, 72, the resultant phase image 73 is a wave with two periods. This, if inversely Fourier transformed, turns into a correlation intensity image 74, thus causing a peak 75 in a position deviated by 2-pixels from a center. This ΔG (pixel) corresponds to a movement amount at a light-receiving surface of a detector. ΔG is transformed into a movement amount Δx on the sample-resting surface. Provided that the diameter of a detector light-emitting surface is L, the magnification of transmission electron microscope on the light-receiving surface is M and the number of pixels on the detector light-receiving surface is Lm, then the movement amount Δx on the sample-resting surface is to be computed by the following Equation (7).

$$\Delta x = \Delta G(\text{pixel}) \times L/Lm(\text{pixel})/M$$ (7)

Δx is a movement amount between the two images 71, 72 on the sample-resting surface. Similarly, computing a movement amount in a Y direction, correction is made by using the electronic sample image moving mechanism shown in FIG. 3 or sample stage shown in FIG. 2 such that the movement amount of between the two images 71, 72 is 0.

(2) Focus Correction

Focus correction will be explained by using a ray diagram shown in FIG. 5. FIG. 5 shows a ray diagram on the cases the objective lens 6 is focused on and off the sample-resting surface 55.

Figure 5A:
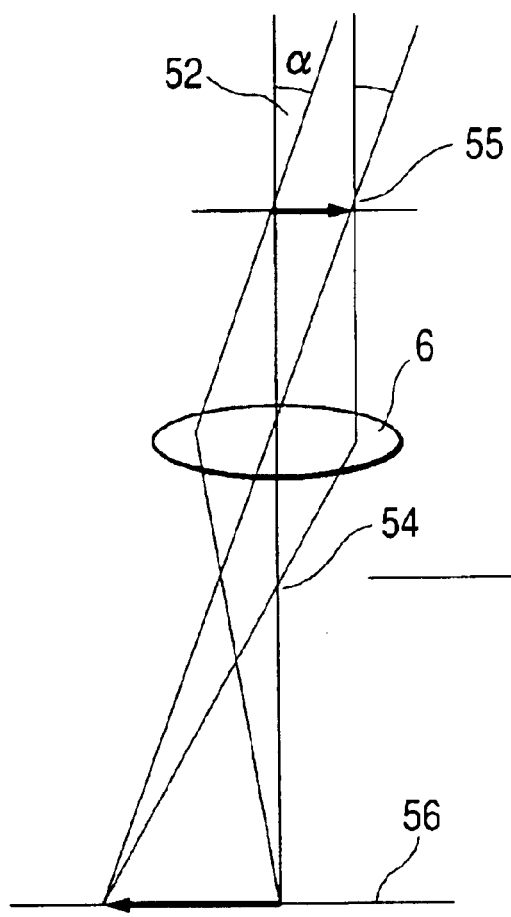
FIGS. 5(a) and 5(b) are ray diagrams of the transmission electron microscope.
Figure 5B:
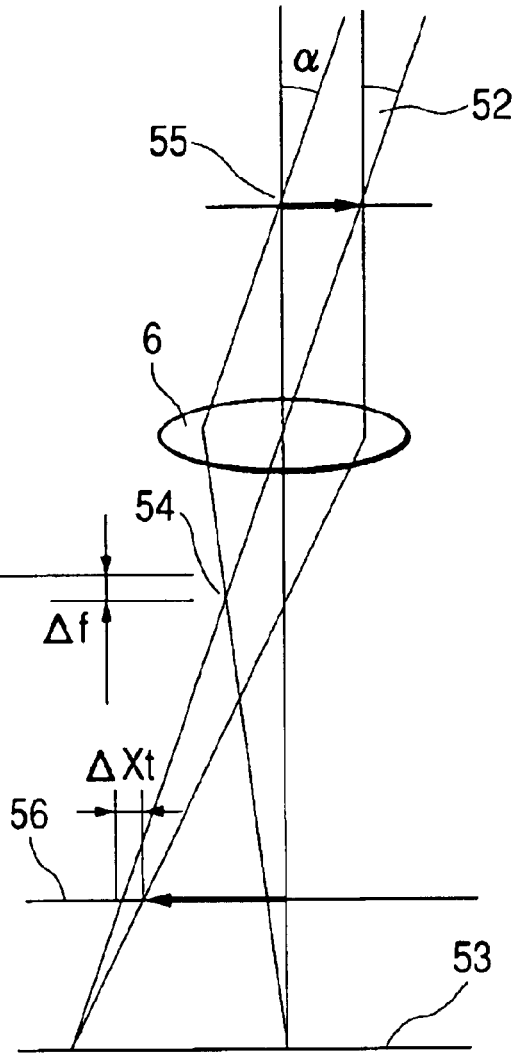

FIG. 5A depicts a case the focus of the objective lens 6 is focused on the sample-resting surface 55. In this case, there is no movement in a transmission electron beam image of a sample formed on an image surface 56 by the objective lens 6 at between an irradiation of an electron beam 52 to the sample at an inclination angle 0 and an irradiation thereof to the sample at an inclination angle α. However, when the objective lens 6 is focused off the sample-resting surface 55, the transmission electron beam image of the sample focuses on a virtual image surface 53 distant from the image surface 56 as shown in FIG. 5B. Accordingly, in case the electron beam 52 irradiated to the sample is inclined from a state of an inclination angle of zero to an inclination angle α, the transmission electron beam image of the sample observed on the image surface 56 moves by ΔXt. By measuring the image movement amount ΔXt, it is possible to compute a defocus amount Δf with respect to a focal point 54.

Figure 6:
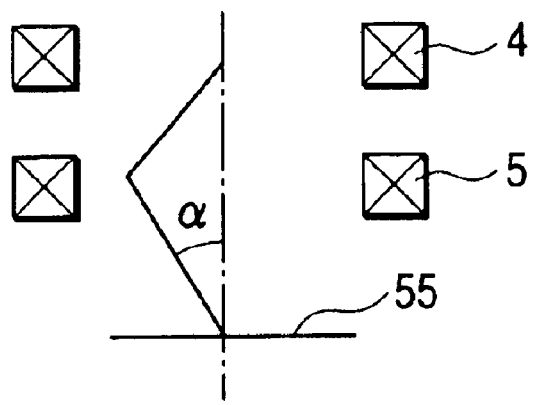
FIG. 6 is an explanatory view of a deflection coil.

Specifically, focus correction is possible by the following operation. The transmission image is recorded as $f1(m, n)$ with the number of pixels M×N to the storage device 36. Next, as shown in FIG. 6, the transmission image in case that an electron beam is irradiated at an inclination angle α to the sample is recorded as $f2(m, n)$ with the number of pixels M×N to the storage device. Similar to the foregoing technique, computed is a movement amount ΔX of between the two images on the sample-resting surface. It is noted that the movement amount ΔX contains an image movement amount δ due to a spherical aberration and hence the movement amount due to defocus is a subtraction of δ from ΔX. δ on the sample-resting surface is expressed as in the following Equation (8) with a spherical aberration Cs and deflection angle α.

$$\delta = Cs \cdot \alpha^3$$ (8)

From the above, the image movement amount ΔXt due to defocus is expressed by the following Equation (9).

$$\Delta Xt = \Delta X - \delta$$ (9)

From the movement amount ΔXt, defocus Δf is to be computed by the following Equation (10).

$$\Delta f = \Delta Xt/\alpha$$ (10)

Next, the defocus amount Δf is converted into an objective current correction value ΔI. Δf and ΔI has a relationship to be expressed in the following Equation (11) by taking C as a constant. Accordingly, by adding an objective current correction value ΔI determined by the relationship of Equation (11) to an objective current value, focus can be adjusted onto the sample.

$$\Delta I = \sqrt{(C/\Delta f)}$$ (11)

Figure 7:
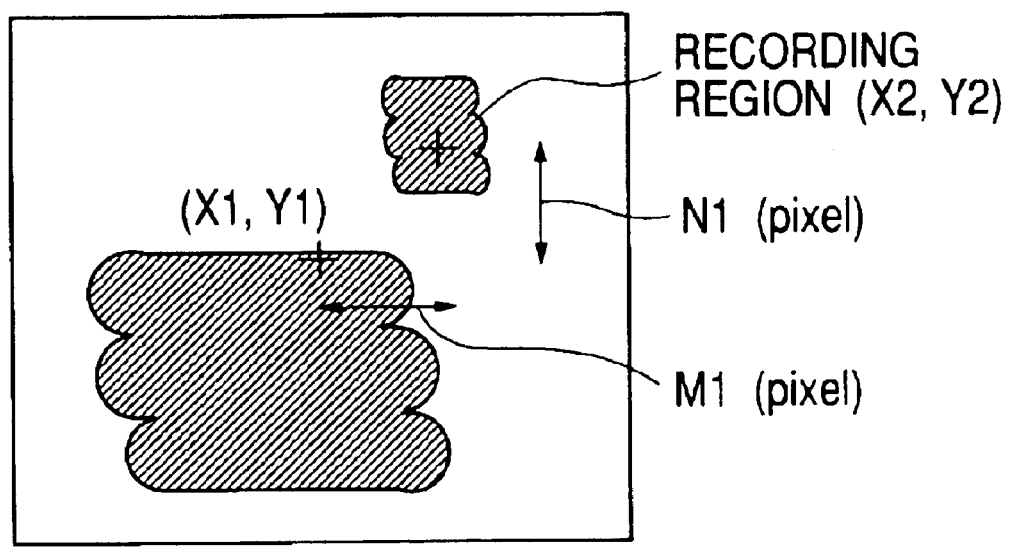
FIG. 7 is an explanatory view of displaying a recording region.

(3) Computing Coordinate on Sample-Resting Surface Corresponding to On-Image Point Meanwhile, the use of Equation (7) makes possible to compute a coordinate (X2, Y2) on the sample-resting surface corresponding to an arbitrary point (M1, N1) on an image. As shown in FIG. 7, an on-image point (M1, N1) can be expressed by a deviation amount of a pixel having an image center as an origin. Provided that the coordinate of an image center on an sample-resting surface is (X1, Y1), the diameter of a detector light-receiving surface is L, a magnification of the transmission electron microscope on the light-receiving surface is M and the number of pixels in the detector light-receiving surface is Lm, then a coordinate (X2, Y2) on the sample-resting surface corresponding to the on-image arbitrary point (M1, N1) is to be expressed by Equation (12).

$$(X2, Y2)=\{X1+M1 \times L/Lm/M, Y1+N1 \times L/Lm\} \tag{12}$$

(4) Displaying Recording Region Over Transmission Image

Using FIG. 7, explanation will be made on a method to superpose and display an observing region over a transmission image 1 in the focus mode provided that the magnification in the observing mode is M and the magnification in the focus mode is Mf. The size {Lfx(pixel), Lfy(pixel)} of an observing region in the focus mode is expressed by the following Equation (13).

$$\{Lfx(\text{pixel}), Lfy(\text{pixel})\}=\{Lm \times M/Mf, Lm \times M/Mf\} \tag{13}$$

Similarly, if taking the magnification in the recording mode Mr, the size {Lrx(pixel), Lry(pixel)} of a recording region over a transmission image acquired in the observing mode is to be expressed by the following Equation (14).

$$\{Lrx, Lry\}=\{Lm \times M/Mr, Lm \times M/Mr\} \tag{14}$$

(5) Coincidence Degree Between Two Images

Figure 8:
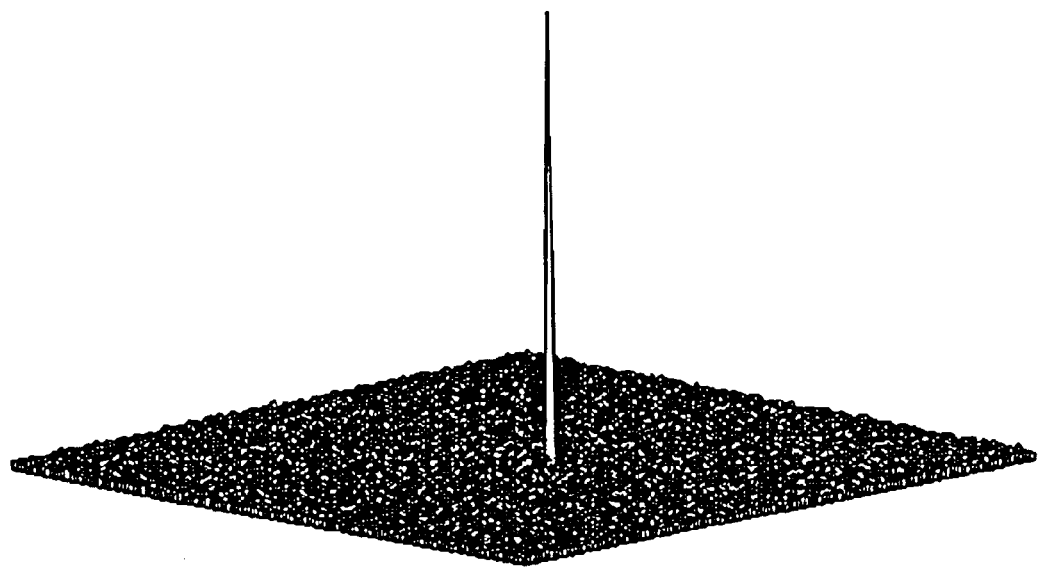
FIG. 8 is an explanatory view of a correlation intensity.

Next, explanation will be made on the accuracy of coincidence between the two images, by using FIG. 8. Because the correlation computation using only a phase component uses mathematically only a phase, the peak appearing in correlation intensity is a δ peak. For example, in case there is deviation by 1.5 pixels between the two images, the composite image has a wave with a 1.5 periods. In case this is inversely Fourier-transformed, a δ peak occurs in a point deviated by 1.5 pixels from a center of a correlation intensity image. However, because there exists no pixel of 1.5, the value at the δ peak is portioned to first and second pixels. Herein, in case a true position of the δ peak is computed from the portioned values by taking a center of gravity on the pixel high in coincidence degree, a computation result is to be obtained to an accuracy of approximately 1/10 pixel. Meanwhile, because the correlation intensity image is due to the δ peak, the similarity between the two images is estimated by a peak height of the correlation intensity image. Provided that the number of image pixels is m×n and the peak height is Peak(pixel), a coincidence degree (%) is to be expressed by the following Equation (15).

$$\text{Coincidence degree } (\%)=(\text{Peak})/(m \times n) \times 100 \tag{15}$$

For example, in the case the number of pixels processed is 128 pixels×128 pixels and Peak is 16384 (pixel), the following is given.

$$\text{Coincident degree}=(16384)/(128 \times 128) \times 100=100(\%)$$

(6) Calculating Recording-Mode Magnification from Size of Recording Region Designated in Observing Mode Next, explanation will be made on a method to calculate a record-region center coordinate and a recording-mode optimal magnification when coordinates are given to the two diagonal apexes of a rectangular region as a record-region designating condition in an observing mode.

From the diagonally-positioned two apexes (M4, N4), (M5, N5) of a rectangular region designated on an image, the number of the pixels Lsx in the X direction of the rectangular region and the number of the pixels Lsy in the Y direction are to be computed by the following Equation (16).

$$\{Lsx, Lsy\}=\{|M5-M4|, |N5-N4|\} \tag{16}$$

An image center (M6, N6) of the recording region is computed from the number of pixels {Lsx, Lsy}. The image center (M6, N6) is as shown in Equation (17) for a case of M5−M4≧0 and N5−N4≧0, Equation (18) for a case of M5−M4<0 and N5−N4≧0, Equation (19) for a case of M5−M4≧0 and N5−N4<0, or Equation (20) for a case of M5−M4<0 and N5−N4<0.

$$(M6, N6)=(M4+(Lsx/2), N4+(Lsy/2)) \tag{17}$$

$$(M6, N6)=(M4-(Lsx/2), N4+(Lsy/2)) \tag{18}$$

$$(M6, N6)=(M4+(Lsx/2), N4-(Lsy/2)) \tag{19}$$

$$(M6, N6)=(M4-(Lsx/2), N4-(Lsy/2)) \tag{20}$$

A coordinate (X6, Y6) on a sample-resting surface corresponding to a recording-area image center (M6, N6) is to be computed by the following Equation (21).

$$(X6, Y7)=\{X1+M6 \times L/Lm/M, Y1+N6 \times L/Lm\} \tag{21}$$

Next, from a region determined by arbitrary points (M4, N4), (M5, N5), computation is made on a magnification M2 for observing that region. Incidentally, shown herein is a case to compute only in the X direction by taking Lsx=Lsy. Provided that the number of pixels on the detector light-receiving surface is Lm, the magnification M2 is to be expressed by Equation (22).

$$M2=Lm/Lsx \tag{22}$$

Explanation will be made herein on an example of a sample observing method using the foregoing element technique.

Figure 10:
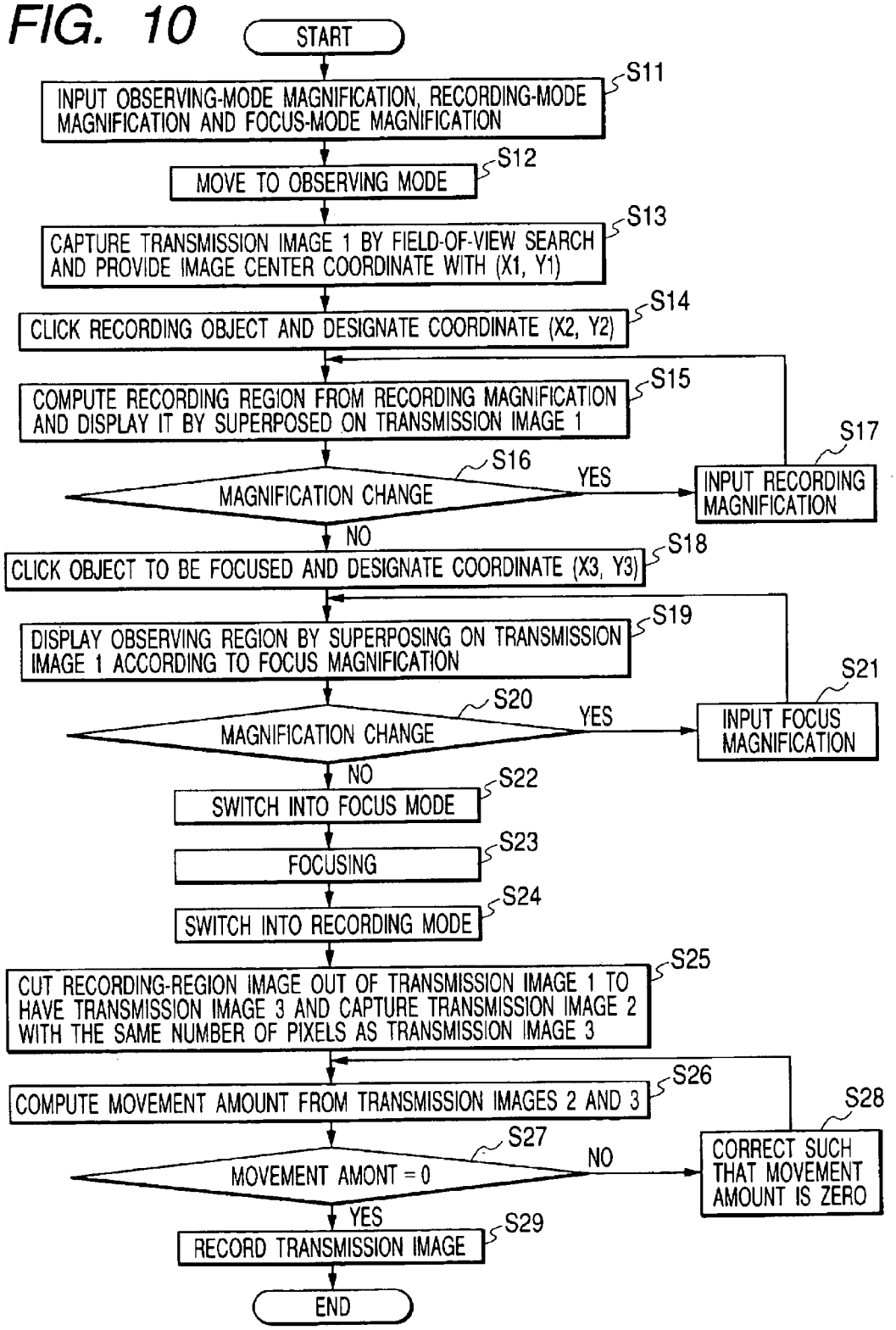
FIG. 10 is a flowchart showing one example of a sample observing procedure according to the invention.

FIG. 10 is a flowchart showing one example of a sample observing procedure according to the invention.

The operator first set a magnification in the observing mode, a magnification in the focus mode and a magnification in the recording mode through a keyboard 44 or magnification-changing rotary encoder 42 (S11). The set magnifications in the respective modes are recorded to the RAM 45.

Next, the operator makes a mode selection by the use of the keyboard 44 or inputting encoder 43, to enter an observing mode (S12). Entering an observing mode, the microprocessor 35 outputs required data out of the lens data previously stored in the ROM 46 to the DACs 24, 25, 28, 31–34 and converts it into an analog signal, such that the transmission electron microscope has a magnification of the observing mode stored in the RAM 45. The DAC 24, 25, 28, 31–34 outputs an analog signal to the excitation power source 13, 14, 17, 20–23, and the excitation power source in turn outputs a current to a lens coil of the corresponding lens system 2, 3, 6, 9–12.

Figure 11:
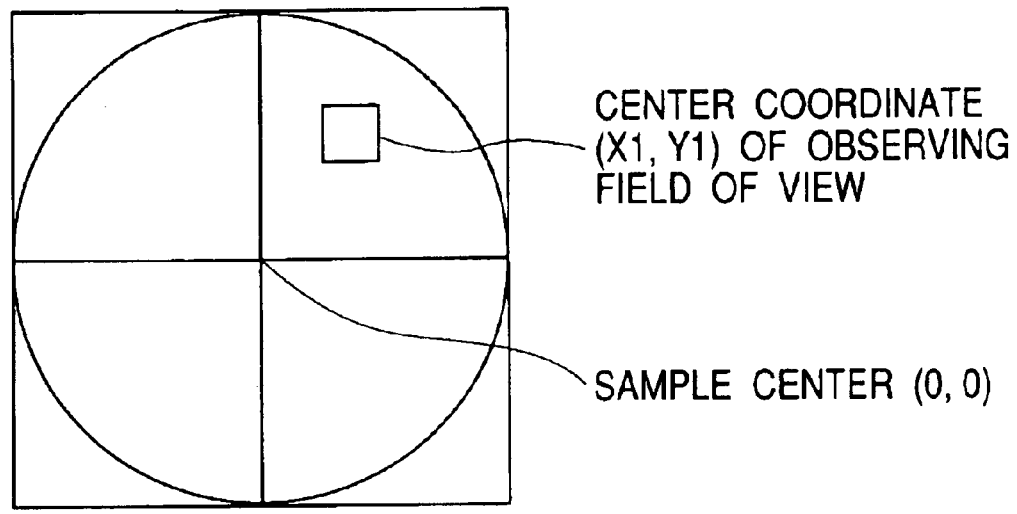
FIG. 11 is a concept view of displaying an observing field of view.

With a desired observing magnification thus set, a magnified transmission image of a sample projected to the scintillator 48 is imaged by the TV camera 49 under control of the TV camera control section 47, and displayed on the CRT 39 through the CRT controller 38. The operator searches a field of view by driving the sample stage 60. In case a field of view including a recording object is found, the image in the view field being imaged by the TV camera 49 is captured by the image-capturing interface 51 and stored as a transmission image 1 in the storage device 36. Next, using the position data of the sample stage, a center coordinate of the view field is stored as a coordinate (X1, Y1) to the storage device 36. At this time, a view field under observation is displayed in position with respect to a sample overall, on a navigation window displayed on the CRT 39, as shown in FIG. 11.

The operator clicks a to-be-recorded object on an image (transmission image 1) displayed on the CRT 39 by the use of the mouse 50, to designate a to-be-recorded region and coordinate thereof. From a mouse-clicked point (M1, N1) on the display image, a corresponding coordinate (X2, Y2) on a sample-resting surface is computed according to the foregoing Equation (12) by the use of the operation processing device 37 (S41).

Next, with the set recording magnification, a recording region {Lrx(pixel), Lry(pixel)} is computed according to the foregoing Equation (14). A frame in a size corresponding to the recording region, superposed over the transmission image 1, is displayed on the CRT 39 (S15). Herein, in such a case that the target object exceeds the recording-mode display region, a recording magnification is inputted, again if required, by using the keyboard 44 or magnification-changing rotary encoder 42, to display a recording-region frame based on a changed recording magnification by superposition over the transmission image 1 (S16, 17).

Figure 12:
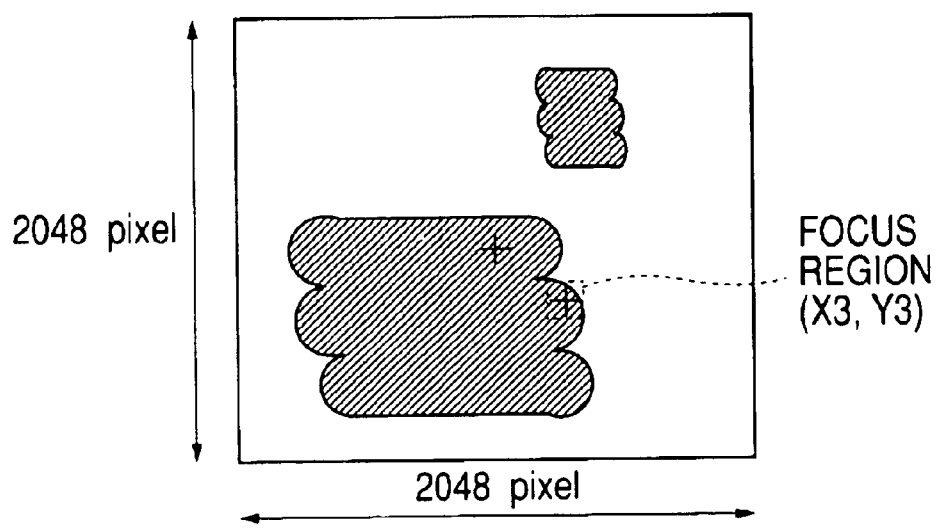
FIG. 12 is an explanatory view of displaying a focus region.

Next, as shown in FIG. 12, the to-be-focused object on the transmission image 1 is clicked by the mouse 50 to designate an on-coordinate position (S18). Similarly to step 14, a coordinate (X3, Y3) on the sample-resting surface corresponding to the point designated over the transmission image 1 is computed by using the operation processing device 37. The computed coordinate (X3, Y3) on the sample-resting surface is stored to the RAM 45. Next, an observing region {Lrx(pixel), Lry(pixel)} is computed by Equation (13) and displayed superposed over the transmission image 1 (S19). In the case of changing the focus-mode magnification, the process moves to step 21 to input a new focus-mode magnification.

Next, the operator uses a keyboard 44 or inputting encoder 43 to make a mode selection, for switching into a focus mode (S22). In case a focus mode is selected, the microprocessor 35 instructs the sample stage controller 57 on the basis of the on-coordinate position (X3, Y3) stored in the RAM 45, to move the sample stage 60 such that the focusing object designated in step 28 is positioned in a view field center. The microprocessor 35 also displays the magnification in the focus mode stored in the RAM 45 on the CRT 39, and makes reference to the lens data stored in the ROM 46 to output required data to the DAC 24, 25, 28, 31–34 such that the transmission electron microscope has a set focus-mode magnification. The DAC 24, 25, 28, 31–34 outputs an analog signal to the excitation power source 13, 14, 17, 20–23. Each of the excitation power source outputs a current to the lens coil of the corresponding lens system 2, 3, 6, 9–12.

Next, focusing is carried out (S23). Focusing can be made by the foregoing procedure. Namely, the transmission image, caused by irradiating an electron beam at an inclination angle of zero to the sample, is recorded as $f1(m, n)$ with the pixels in the number of M×N to the storage device, while the transmission image, caused by irradiation at an inclination angle of a, is recorded as $f2(m, n)$ with the pixels in the number of M×N to the storage device. Then, computed is a movement amount (deviation amount) $\Delta x$ of between the two images $f1(m, n)$, $f2(m, n)$ on the sample-resting surface. On the basis of the movement amount $\Delta x$, an objective current correction value $\Delta I$ is determined according to the foregoing Equations (8)–(11). Then, a determined objective current correction value $\Delta I$ is added to the objective current value. Due to this, focusing is made possible onto the sample.

The electron beam irradiation at an angle of $\alpha$ can be made by outputting from the ROM 46 to the DAC 26, 27 the deflection data in a case that an electron beam is inclined to a deflection angle $\alpha$ by two-staged deflection coils 4, 5 and outputting an analog signal from the DAC 26, 27 to the excitation power source 15, 16 to flow a current to the deflection coil 4, 5. Also, the objective current correction value $\Delta I$ is outputted to the DAC 28 to convert the lens data into an analog signal. The DAC 28 outputs an analog signal to the excitation power source 17 to output a current to the objective lens coil 6.

Then, the operator makes a mode selection by using the keyboard 44 or inputting encoder 43, for switching into a recording mode (S24). In case a recording mode is selected, the microprocessor 35 instructs the sample stage controller 57 to move the sample stage 60 such that the coordinate (X2, Y2) on the sample-resting surface stored in the RAM 45 is positioned in a view field center. The microprocessor 35 also displays the recording-mode magnification stored in the RAM 45 on the CRT 39 by the use of the CRT controller 38. Simultaneously, the required data of the lens data stored in the ROM 46 is outputted to the DAC 24, 25, 28, 31–34 such that the transmission electron microscope has the recording-mode magnification. The DAC 24, 25, 28, 31–34 outputs an analog signal to the excitation power source 13, 14, 17, 20–23. The excitation power source outputs a current to the lens coil of the corresponding lens system 2, 3, 6, 9–12, thereby realizing the set magnification.

In the next step 25, an image in the recording area computed in the step 15 is cut out of the transmission image 1 and stored as a transmission image 3 to the RAM 45. Also, the high-magnification transmission image, projected by using the TV camera control section 47 to the scintillator 48, is captured by the TV camera 49 and stored as a transmission image 2 having the same number of pixels as the transmission image 3 to the storage device 36 by the image-capturing interface 51. In order to make same the number of pixels of the transmission image 2 as the number of pixels of the transmission image 3, a binning process is carried out.

Then, computed is a movement amount of the transmission image 2 and transmission image 3 by using the operating device 37 (S26). Specifically, the transmission image 2 and the transmission image 3 are compared according to the method explained by the foregoing Equations (1) to (7), to compute a positional deviation (movement amount) of between the transmission image 2 and the transmission image 3. In the case that the movement amount is not zero, the microprocessor 35 makes a correction to render the movement amount zero (S27, S28). Specifically, the data required for moving the transmission image 3 to an image center is sent to the DAC 29, 30 depending on the movement amount computed in the step 26. The electromagnetic sample image moving coil 7, 8 is energized by the excitation power source 18, 19 to move a sample magnified image projected to the scintillator 48. Otherwise, instruction is made to the sample stage controller 57 to move the sample stage 60 such that the transmission image 3 positions in the image center.

In case the movement amount is zero in the determination of step 27, the recording-object magnified image designated in the step 24 is coincident with the view field center. Thus, the process proceeds to the next step 29 to record the transmission image. In this manner, even if there is difference in transmission electron microscope magnification in between the observing mode for view-field search and the recording mode for magnified transmission image recording, the recording object designated in the observing mode can be automatically positioned to the view field center to image and record a high-magnification image thereof. Incidentally, in the step 27, a coincidence degree also may be computed by Equation (15) to determine a reliability of a movement amount value depending on a coincidence degree. For example, in the case the coincidence degree is extremely small despite the movement amount is zero, there is a possibility that the transmission image 2 and the transmission image 3 are images at quite different sites. Accordingly, a threshold may be set to an incident degree so that, when the coincident degree computed in the step 27 is smaller than a set threshold, the ordinary process is suspended to sound or display an alarm. Also in the other embodiment referred later, determination may be simultaneously made also on coincidence degree upon determining whether the movement amount is zero or not so that a similar measure can be taken when coincidence degree is low.

Figure 13:
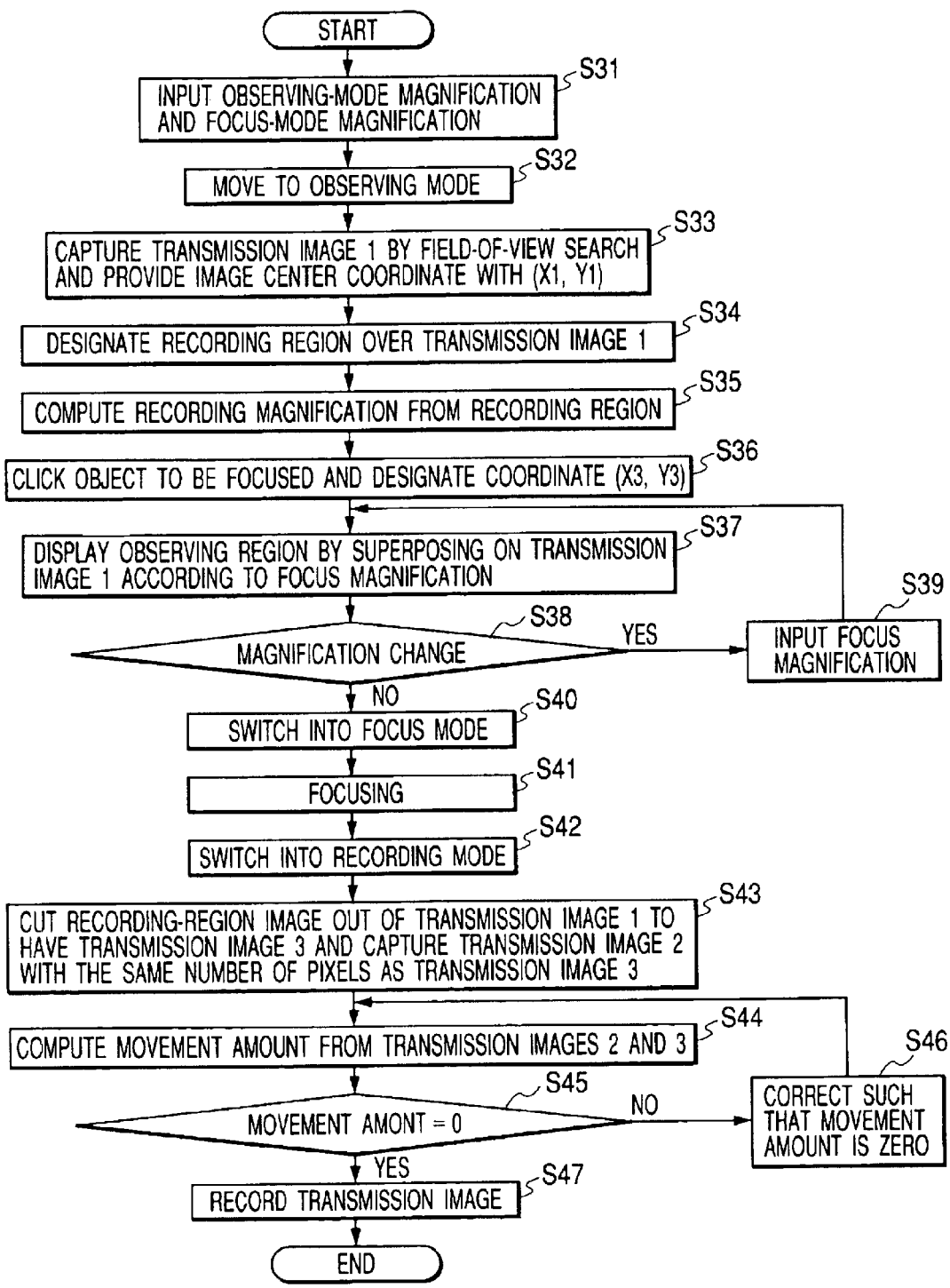
FIG. 13 is a flowchart showing another example of a sample observing procedure according to the invention.

FIG. 13 is a flowchart showing another example of a sample observing procedure according to the invention. This sample observing procedure is different from the procedure explained in FIG. 10 in that the magnification in the recording mode is automatically determined without making a designation. In the other respect, this is substantially similar to FIG. 10. Explanation will be herein made only on the points different from FIG. 10.

The operator first sets observation-mode and focus-mode magnifications by the use of the keyboard 44 or magnification-changing rotary encoder 42 (S31). The magnifications in the modes thus set are stored to the RAM 45. The processes of steps 32 and 33 are substantially the same as the processes explained concerning the steps 12 and 13 of FIG. 10.

Figure 9:
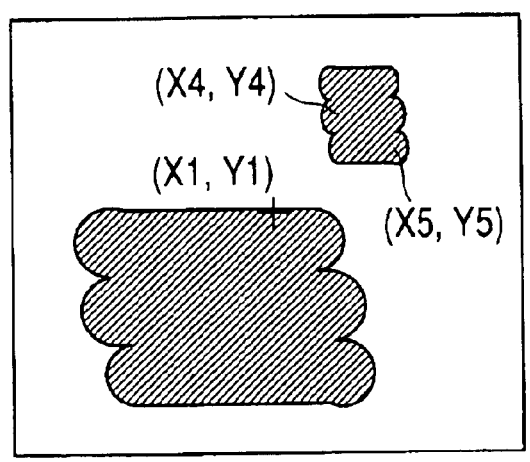
FIG. 9 is an explanatory view of a method to designate a recording region.

Next, the operator designates a recording region over the transmission image 1 by the use of a mouse or the like (S34). Designating a recording region can be made by designating two diagonally-positioned apexes of a rectangular surrounding the recording region, e.g. upper left and lower right corners or upper right and lower left corners of a rectangular recording region, as shown in FIG. 9. Next, from a size of the designated recording region, computed is a maximum magnification for imaging a magnified image of the region entirety by the TV camera 49, i.e. a recording-mode magnification (S35). The recording-mode magnification can be computed by the method explained using the foregoing Equations (16) to (22). The recording-mode magnification M2 computed by Equation (22) is stored to the RAM 45.

The focusing process to be made in the following steps 36 to 41 is substantially the same as the process explained concerning the steps 18 to 23 of FIG. 10. The recording-mode process in steps 42 to 46 and transmission image recording process in step 47, after ending the focusing, is substantially the same as the process explained concerning the steps 24 to 29 of FIG. 10 except for the difference of whether the recording-mode magnification recorded in the RAM 45 has been set by the operator (FIG. 10 case) or automatically set/stored by the device (FIG. 13 case).

In this manner, even by the sample observing procedure shown in FIG. 13 without designating a recording-mode magnification, even where there is difference in transmission electron microscope magnification in between the observing mode for view field search and the recording mode for magnified transmission image recording, the recording object designated in the observing mode can be automatically positioned in a view field center to image and record a high-magnification image thereof.

Figure 14:
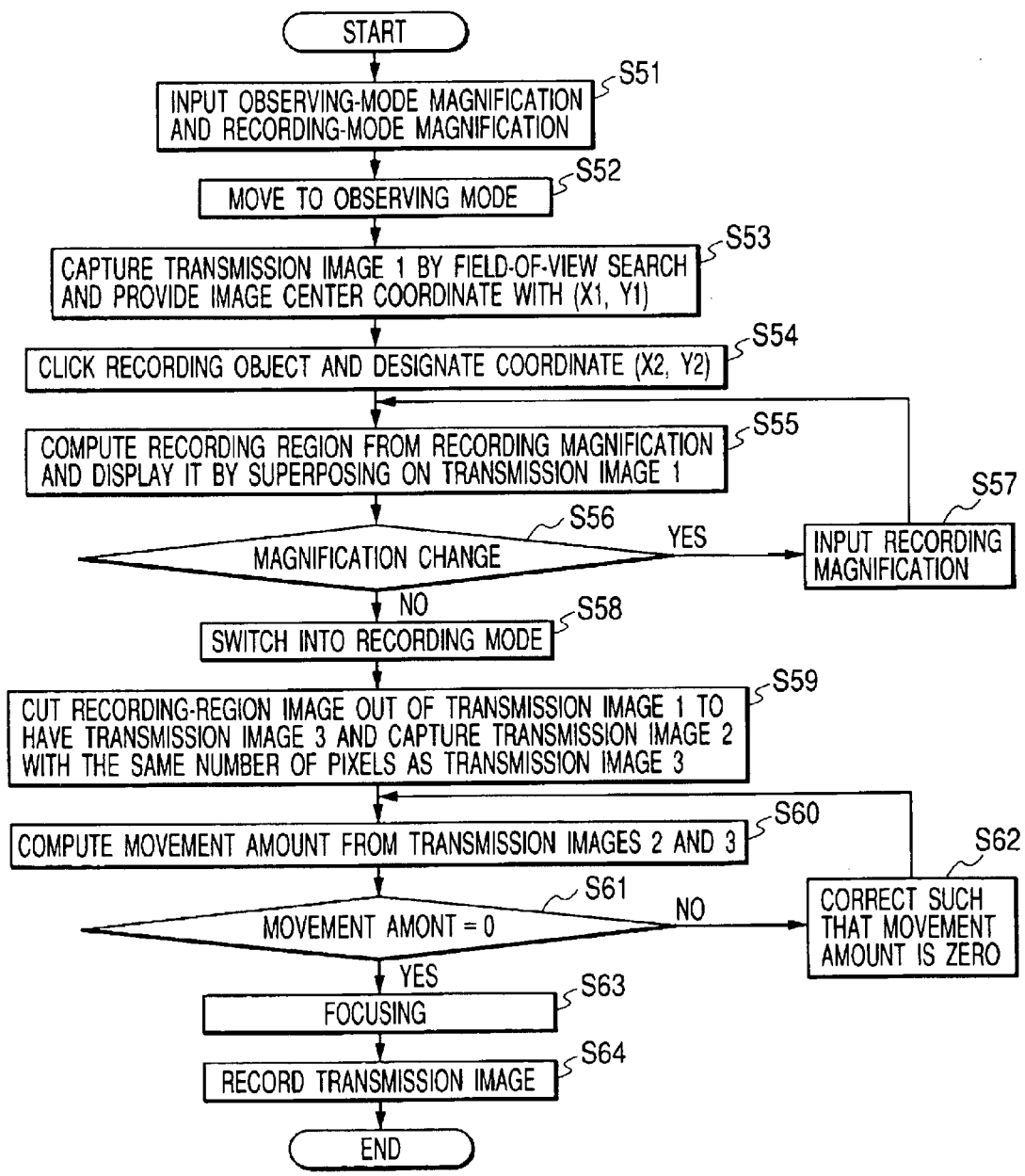
FIG. 14 is a flowchart showing still another example of a sample observing procedure according to the invention.

FIG. 14 is a flowchart showing still another example of a sample observing procedure according to the invention. In the sample observing procedure so far explained according to FIG. 10 or 13, focusing is first made, and then the magnification of the transmission electron microscope was set to a recording-mode magnification to correct the movement amount of a sample image with respect to a view field center such that the high-magnification image in a recording region was positioned in the view field center. On the contrary, the sample observing procedure to be explained herein is an example that the transmission electron microscope is set to a recording-mode magnification whereby a movement amount of a sample image with respect to a view field center is first corrected such that a high-magnification image in a recording region positions in a view field center, and then focusing is made while maintaining the recoding-mode magnification.

The operator first sets observing-mode and recording mode magnifications through the keyboard 44 or magnification-changing rotary encoder 42 (S51). The set magnification of the modes are stored to the RAM 45.

Next, the operator makes a mode selection by the use of the keyboard 44 or inputting encoder 43, to enter in an observing mode (S52). When the observing mode is entered, the microprocessor 35 outputs required data out of the lens data previously stored in the ROM 46 to the DACs 24, 25, 28, 31–34 such that the transmission electron microscope has an observing-mode magnification stored in the RAM 45, and converts it into an analog signal. The DAC 24, 25, 28, 31–34 outputs an analog signal to the excitation power source 13, 14, 17, 20–23, and the excitation power source in turn outputs a current to a lens coil of the corresponding lens system 2, 3, 6, 9–12.

With a desired observing magnification thus set, a magnified transmission image of a sample projected to the scintillator 48 is imaged by the TV camera 49 under control of the TV camera control section 47, and displayed on the CRT 39 through the CRT controller 38. The operator searches a field of view by driving the sample stage 60. In case a field of view including a recording object is found, the image in the view field being imaged by the TV camera 49 is captured by the image-capturing interface 51 and stored as a transmission image 1 in the storage device 36. Next, using the position data of the sample stage, a center coordinate of the view field is stored as a coordinate (X1, Y1) to the storage device 36 (S53).

The operator clicks a to-be-recorded object over an image (transmission image 1) displayed on the CRT 39 by the use of the mouse 50 as shown in FIG. 7, to designate a to-be-recorded region and coordinate position thereof. From a mouse-clicked point (M1, N1) on the display image, a corresponding coordinate (X2, Y2) on a sample-resting surface is computed according to the foregoing Equation (12) by the use of the operation processing device 37 (S54).

Next, with the set recording magnification, a recording region {Lrx(pixel), Lry(pixel)} is computed according to the foregoing Equation (14). A frame having a size corresponding to the recording region, superposed on the transmission image 1, is displayed on the CRT 39 (S55). Herein, in such a case that the target object exceeds the recording-mode display region, a recording magnification is inputted, again if required, by using the keyboard 44 or magnification-changing rotary encoder 42, to display a frame of the recording region based on a changed recording magnification by superposition on the transmission image 1 (S56, 57).

Then, the operator makes a mode selection by using the keyboard 44 or inputting encoder 43, for switching into a recording mode (S58). In case a recording mode is selected, the microprocessor 35 instructs the sample stage controller 57 to move the sample stage 60 such that the coordinate (X2, Y2) on the sample-resting surface stored in the RAM 45 is positioned in a view field center. The microprocessor 35 also displays on the CRT 39 the recording-mode magnification stored in the RAM 45 by the use of the CRT controller 38. Simultaneously, the required data of the lens data stored in the ROM 46 is outputted to the DAC 24, 25, 28, 31–34 such that the transmission electron microscope has the recording-mode magnification set before. The DAC 24, 25, 28, 31–34 outputs an analog signal to the excitation power source 13, 14, 17, 20–23. The excitation power source outputs a current to the lens coil of the corresponding lens system 2, 3, 6, 9–12 thereby realizing a set magnification.

In the next step 59, an image in the recording area computed in the step 55 is cut out of the transmission image 1 and stored as a transmission image 3 to the RAM 45. Also, the high-magnification transmission image, projected by using the TV camera control section 47 to the scintillator 48, is captured by the TV camera 49 and stored as a transmission image 2 having the same number of pixels as the transmission image 3 to the storage device 36 by the image-capturing interface 46. In order to make same the number of pixels of the transmission image 2 as the number of pixels of the transmission image 3, a binning process is carried out.

Then, computed is a movement amount of the transmission image 2 and transmission image 3 by using the operating device 35 (S60). Specifically, the transmission image 2 and the transmission image 3 are compared according to the method explained by the foregoing Equations (1) to (7), to compute a positional deviation (movement amount) of between the transmission image 2 and the transmission image 3. In computing a deviational amount (movement amount) of between the two images, perfect focusing is not necessarily required. In the case that the movement amount is not zero, the microprocessor 35 makes a correction to render the movement amount zero (S61, S62). Specifically, the data required for moving the position of the transmission image 3 to an image center is sent to the DAC 29, 30 depending on the movement amount computed in the step 60. The electromagnetic sample image moving coil 7, 8 is energized by the excitation power source 18, 19 to move a sample magnified image to be projected to the scintillator 48. Otherwise, instruction is made to the sample stage controller 57 to move the sample stage 60 such that the transmission image 3 comes to the image center.

In case the movement amount is zero in the determination of step 61, the recording-object magnified image designated in the step 54 is coincident with a view field center. Thus, the process proceeds to the next step 63 to carry out focusing. Although focusing may be manual, it may be automatically made by the foregoing method. Namely, the transmission image, caused by irradiating an electron beam at an inclination angle of zero to the sample, is recorded as $f1(m, n)$ with the pixels in the number of M×N to the storage device, while the transmission image, caused by irradiation at an inclination angle of α, is recorded as $f2(m, n)$ with the pixels in the number of M×N to the storage device. Computed is a movement amount (deviation amount) Δx between the two images $f1(m, n)$, $f2(m, n)$ on the sample-resting surface. On the basis of the movement amount Δx, an objective current correction value ΔI is determined according to the foregoing Equations (8)–(11). Then, a determined objective current correction value ΔI is added to the objective current value. Due to this, focusing is made possible onto the sample.

Finally, in step 64, the transmission image is recorded. In this manner, even if there is difference in transmission electron microscope magnification in between the observing mode for view-field search and the recording mode for magnified transmission image recording, the recording object designated in the observing mode can be automatically positioned in the view field center to image and record a high-magnification image thereof.

Figure 15:
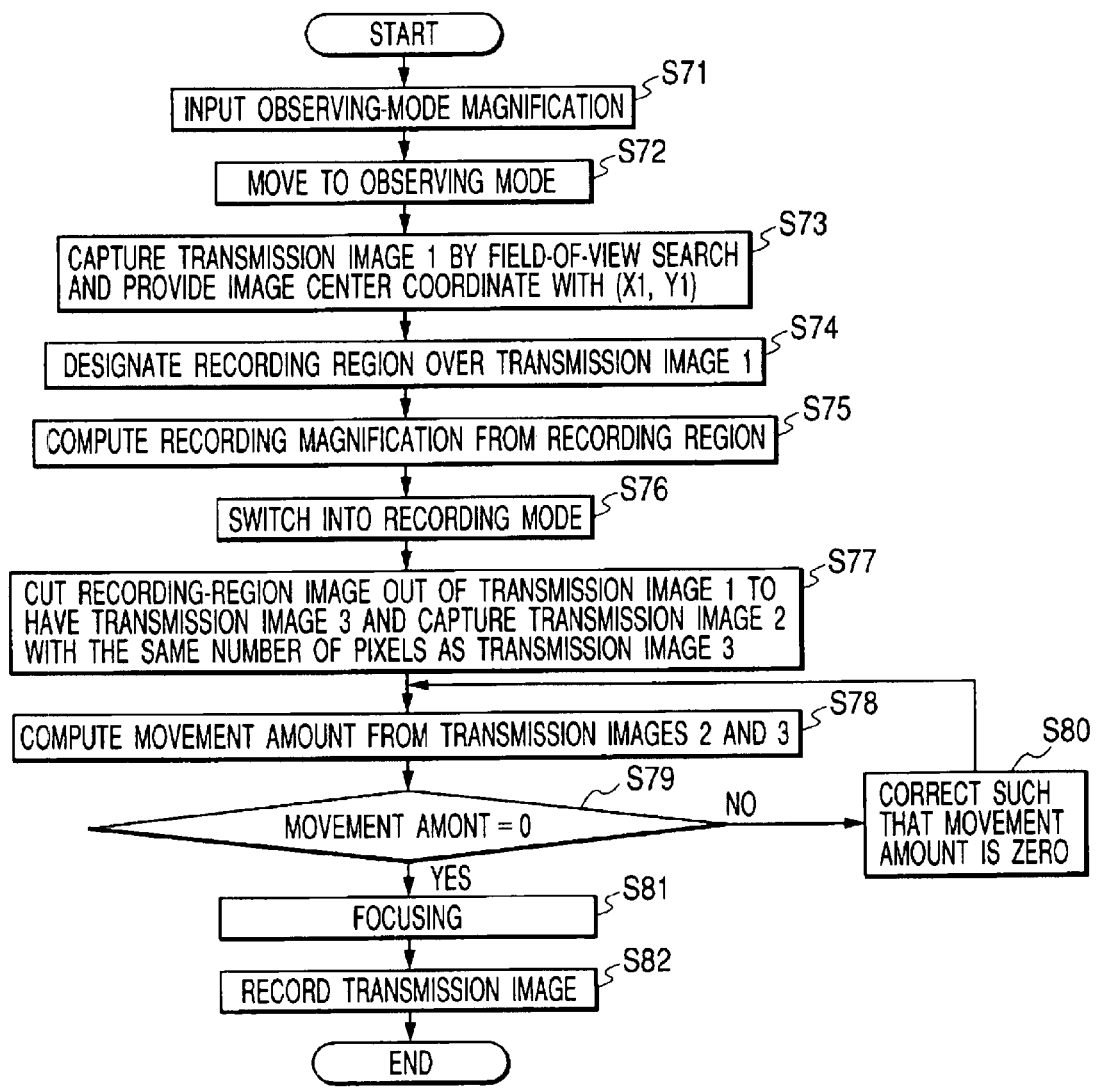
FIG. 15 is a flowchart showing another example of a sample observing procedure according to the invention.

FIG. 15 is a flowchart showing another example of a sample observing procedure according to the invention. This sample observing procedure is different from the procedure explained in FIG. 14 in that determination is automatic without designating a recoding-mode magnification. The other major points are substantially the same as those of FIG. 14. Herein, the processes same as the processes explained in FIG. 14 are omitted in duplicated explanation by quoting them.

The operator first sets an observing-mode magnification by using the keyboard 44 or magnification-changing rotary encoder 42 (S71). The set magnification is stored to the RAM 45. The processes in steps 72 and 73 are substantially the same as the processes explained concerning the steps 52 and 53 of FIG. 14.

Next, the operator designates a recording region over the transmission image 1 (S74). Designating a recording region can be made by designating two diagonally-positioned apexes of a rectangular surrounding the recording region, e.g. upper left and lower right corners or upper right and lower left corners of a rectangular recording region, as shown in FIG. 9. Next, from a size of the designated recording region, computed is a maximum magnification for imaging a magnified image of the region entirety by the TV camera 49, i.e. a recording-mode magnification (S75). The recording-mode magnification can be computed by the method explained using the foregoing Equations (16) to (22). The recording-mode magnification M2 computed by Equation (22) is stored to the RAM 45.

The process in the recording mode to be made in the following steps 76 to 80 are substantially the same as the process explained concerning the steps 24 to 29 of FIG. 10, except for the difference of whether the recording-mode magnification recorded in the RAM 45 has been set by the operator (FIG. 14 case) or automatically set/stored by the device (FIG. 15 case). Also, the focusing process to be made in step 81 is substantially the same as the process explained concerning the step 63 of FIG. 14. Finally, recorded is a high-magnification transmission electron beam image of the sample in the recording region in step 82.

In this manner, even by the sample observing procedure shown in FIG. 15 without designating a recording-mode magnification, the recording object designated in the observing mode can be automatically positioned in a view field center to image and record a high-magnification image thereof.

Figure 16:
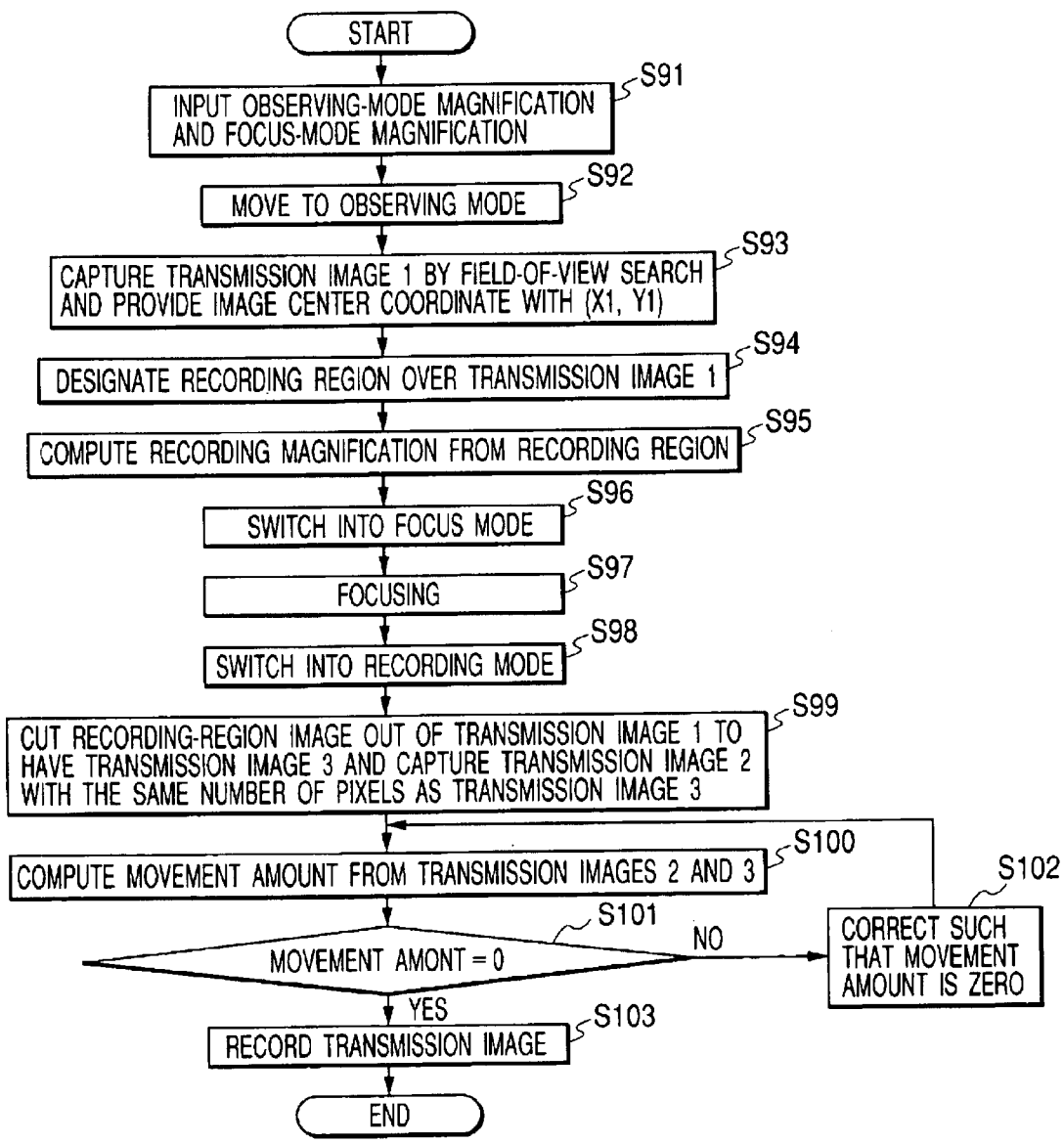
FIG. 16 is a flowchart showing another example of a sample observing procedure according to the invention.

FIG. 16 is a flowchart showing another example of a sample observing procedure according to the invention. This sample observing procedure is different from the sample observing procedure explained in FIG. 15 in that the focusing process (steps 96, 97) is carried out prior to the switching to a recording mode (step 98). The content of the other processes is substantially the same as the processes so far explained using FIGS. 10, 13 and 14, and hence omitted in duplicated explanation by quoting the corresponding step numbers.

The operator first sets the magnifications in the observing and focusing modes by using the keyboard 44 or magnification-changing rotary encoder 42 (S91). The set magnifications are stored to the RAM 45. The subsequent process of steps 92 to 95 is the substantially the same as the process explained concerning the steps 72 to 75 of FIG. 15.

Next, the operator makes a mode selection by the use of the keyboard 44 or inputting encoder 43, thereby making switching into a focus mode (S96) for carrying out focus adjustment (S97). The process content of the steps 96, 97 is substantially the same as the process content explained concerning the steps 22, 23 of FIG. 10, for example.

The operator then makes switching into a recording mode (S98) to carry out a process concerning the movement correction to a magnified image, thereafter recording the transmission image. The process content of steps 98 to 103 is substantially the same as the process content explained concerning the steps 42 to 47 of FIG. 13, for example.

According to the present invention, sample positioning is possible with accuracy in the transmission electron microscope, facilitating sample observation using the transmission electron microscope.

What is claimed is:

1. A method of observing a sample by a transmission electron microscope comprising:

a step of inputting a first magnification for use in searching a field of view and a second magnification for use in recording;

a step of setting a magnification of a transmission electron microscope to the first magnification;

a step of imaging a transmission electron beam image of a sample held on a sample stage by imaging means and displaying the transmission electron beam image of the sample in the first magnification on an image display section;

a step of computing and storing a sample stage coordinate of a subject of recording designated over the transmission electron beam image of the sample displayed on the image display section;

a step of cutting an image of the subject of recording out of the transmission electron beam image of the sample in the first magnification and storing a cut-out image as a first image;

a step of setting the magnification of the transmission electron microscope to the second magnification;

a step of moving the sample stage to the stored sample stage coordinate of the subject of recording;

a step of capturing the transmission electron beam image in the second magnification with the same number of pixels as the first image and storing a captured image as a second image;

a step of computing a movement amount of between two images from a correlation intensity of the first and second images;

a step of correcting a position of the transmission electron beam image in the second magnification with respect to the imaging means such that the movement amount is zero; and a step of recording the transmission electron beam image in the second magnification imaged by the imaging means.

2. A method of observing a sample according to claim 1, further comprising a step of computing a size of a region on the sample to be recorded in the second magnification over the transmission electron beam image of the sample in the first magnification, and a step of displaying a mark representing a region in a computed size by being superposed over a corresponding area of the transmission electron beam image in the first magnification.

3. A method of observing a sample by a transmission electron microscope comprising;

a step of inputting a first magnification for use in searching a field of view;

a step of setting a magnification of a transmission electron microscope to the first magnification;

a step of imaging a transmission electron beam image of a sample held on a sample stage by imaging means and displaying the transmission electron beam image in the first magnification on an image display section;

a step of acquiring information concerning a recording region designated over the transmission electron beam image of the sample displayed on the image display section;

a step of computing and storing a sample stage coordinate of the recording region and a second magnification capable putting the recording region fully iii a field of view form the acquired information;

a step of cutting an image in the recording region out of the transmission electron beam image of the sample in the first magnification end storing a cut-out image as a first image;

a step of setting the magnification of the transmission electron microscope to the second magnification;

a step of moving the sample stage to the stored sample stage coordinate of the recording region;

a step of capturing the transmission electron beam image in the second magnification with the same number of pixels as the first image and storing a captured image as a second image;

a step of computing a movement amount of between the two images from a correlation intensity of the first and second images;

a step of correcting a position of the transmission electron beam image in the second magnification with respect to the imaging means such that the movement amount is zero; and a step of recording the transmission electron beam image in the second magnification imaged by the imaging means.

4. A method of observing a sample according to any one of claims 1 to 3, wherein the position of the transmission electron beam image in the second magnification with respect to the imaging means is corrected by moving the sample stage or deflecting an electron beam transmitted through the sample with using a sample image moving coil.

5. A method of observing a sample according to claim 4, further comprising a step of determining a movement amount of an image when an electron beam irradiated to the sample is inclined by a predetermined angle, and a step of correcting an objective current value on the basis of the movement amount of the image and thereby correcting for focusing of an objective lens.

6. A method of observing a sample according to claim 5, wherein a movement amount of between the two images is displayed.

7. A transmission electron microscope comprising:

an electron gun for emitting an electron beam;

an irradiation lens for converging the electron beam;

a sample stage for holding a sample irradiated with the converged electron beam;

a projection lens for forming a sample transmission electron image;

an image device for imaging the transmission electron image;

an operating device fix capturing a second image in a second magnification having a number of pixels corresponding to a number of pixels of a first image which is cut our from a part of the transmission electron image captured in a first magnification, and computing a movement amount between the two images from a correlation intensity of the first and second images.

* * * * *